US008124165B2

(12) United States Patent
Tsai

(10) Patent No.: US 8,124,165 B2
(45) Date of Patent: Feb. 28, 2012

(54) PRESSURIZED DIP COATING SYSTEM

(75) Inventor: Steve Tsai, Stamford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 1403 days.

(21) Appl. No.: 11/711,253

(22) Filed: Feb. 26, 2007

(65) Prior Publication Data

US 2007/0200267 A1 Aug. 30, 2007

Related U.S. Application Data

(60) Provisional application No. 60/777,055, filed on Feb. 27, 2006.

(51) Int. Cl.
*B05D 3/02* (2006.01)
*B05D 1/18* (2006.01)
*A61B 17/04* (2006.01)

(52) U.S. Cl. ................... 427/2.1; 427/430.1; 427/434.5; 427/2.3; 427/2.31; 427/2.24; 118/40; 118/500; 606/230

(58) Field of Classification Search ............... 427/430.1, 427/434.5, 2.1–2.31; 118/40, 500; 606/230–232
See application file for complete search history.

(56) References Cited

U.S. PATENT DOCUMENTS 2,554,254 A * 5/1951 Kroft ............................ 427/595
2,734,506 A * 2/1956 Nichols et al. ................ 606/230
3,449,152 A 6/1969 Detrick et al.
3,746,253 A 7/1973 Walberg
4,027,676 A 6/1977 Mattei
4,043,344 A 8/1977 Landi et al.
4,047,533 A 9/1977 Perciaccante et al.
4,105,034 A 8/1978 Shalaby et al.
4,109,609 A * 8/1978 Hunter ............................ 118/50
4,185,637 A 1/1980 Mattei
4,201,216 A 5/1980 Mattei
4,384,014 A 5/1983 Young
4,532,929 A 8/1985 Mattei et al.
4,911,927 A 3/1990 Hill et al.
5,104,398 A 4/1992 Planck et al.
5,152,782 A 10/1992 Kowligi et al.
5,171,613 A 12/1992 Bok et al.
5,312,642 A 5/1994 Chesterfield et al.
5,508,060 A 4/1996 Perman et al.
5,786,022 A 7/1998 Agarwal et al.
5,817,129 A 10/1998 Labrecque et al.
6,187,095 B1 2/2001 Labrecque et al.
6,383,229 B2 5/2002 Entrekin et al.
6,451,373 B1 9/2002 Hossainy et al.
6,506,437 B1 1/2003 Harish et al.
6,534,112 B1 3/2003 Bouchier et al.

(Continued)

FOREIGN PATENT DOCUMENTS

DE 1 771 354 A1 12/1971

(Continued)

OTHER PUBLICATIONS

European Search Report from Application EP 06 02 6288 dated Mar. 29, 2007.

(Continued)

*Primary Examiner* — Timothy Meeks
*Assistant Examiner* — Cachet Sellman

(57) ABSTRACT

The present disclosure provides a method and apparatus for coating a medical device.

18 Claims, 2 Drawing Sheets

U.S. PATENT DOCUMENTS

| | | | | |
|---|---|---|---|---|
| 6,712,838 | B2 * | 3/2004 | D'Aversa et al. | 606/230 |
| 2002/0168394 | A1 | 11/2002 | Hossainy et al. | |
| 2004/0033306 | A1 | 2/2004 | Bouchier et al. | |
| 2004/0040500 | A1 | 3/2004 | Bouchier et al. | |
| 2004/0047978 | A1 | 3/2004 | Hossainy et al. | |
| 2006/0029722 | A1 | 2/2006 | Larson et al. | |
| 2006/0193890 | A1 * | 8/2006 | Owens et al. | 424/423 |

FOREIGN PATENT DOCUMENTS

| | | | |
|---|---|---|---|
| DE | 17 71 354 | | 12/1971 |
| DE | 40 31 437 | | 4/1992 |
| DE | 40 31 437 | A1 | 4/1992 |
| EP | 0 839 542 | A2 | 5/1994 |
| EP | 1 074 270 | A1 | 2/2001 |
| WO | WO 82 03030 | | 9/1982 |
| WO | WO 86/00020 | A1 | 1/1986 |

OTHER PUBLICATIONS

European Search Report (EP 07 00 3136 dated Jun. 27, 2007).

European Search Report from European Patent Application No. EP 07 00 3136 dated Jun. 20, 2007.

* cited by examiner

PRESSURIZED DIP COATING SYSTEM

CROSS-REFERENCE TO RELATED APPLICATION

The present application claims the benefit of and priority to U.S. Provisional Application Ser. No. 60/777,055, filed on Feb. 27, 2006, the entire disclosure of which is incorporated herein by reference.

BACKGROUND

1. Technical Field

The present disclosure relates to a method for coating a medical device such as a braided suture and an apparatus for coating a medical device.

2. Background of Related Art

Medical devices intended for the repair of body tissues must meet certain requirements: they must be substantially non-toxic, capable of being readily sterilized, they must have good tensile strength and if they are of the absorbable or biodegradable variety, the absorption or biodegradation of the device must be closely controlled. An example of a particularly useful medical device is sutures.

Sutures have been constructed from a wide variety of materials including surgical gut, silk, cotton, a polyolefin such as polypropylene, polyamide, polyglycolic acid, polyesters such as polyethylene terephthalate and glycolide-lactide copolymer, etc. Some materials are suitable for preparing monofilament sutures, while sutures manufactured from other materials are provided as braided structures. For example, sutures manufactured from silk, polyamide, polyester and bioabsorbable glycolide-lactide copolymer are usually provided as multifilament braids.

Currently available braided suture products are acceptable in terms of their tensile strength and ability to be sterilized. However, they can be difficult to coat from a processing standpoint due to the small interstitial spaces present between each individual filament that may be difficult to penetrate.

It would be advantageous to have more effective methods for coating medical devices, especially multifilament medical devices.

SUMMARY

Methods are described wherein medical devices are coated in a pressurized system. The process includes the steps of placing one or more medical devices to be coated into a coating vessel and reducing the pressure within the vessel. A coating composition is added to the vessel to contact the medical device with the coating composition. Next, the pressure inside the vessel is increased. The coating composition is optionally withdrawn from and re-introduced into the vessel via a circulation pump. After the medical device contacts the coating composition for a predetermined amount of time, the vessel is drained and any excess coating composition is collected in a reservoir. Pressure within the vessel is again reduced and, optionally, a heated inert gas is passed through the vessel to cure the coating and/or dry the medical device. The coated medical device can then be removed from the vessel. Apparatus for performing the present methods are also described herein.

DETAILED DESCRIPTION

The present methods can be used to coat any medical device. Some examples include, but are not limited to, sutures, staples, meshes, stents, grafts, clips, pins, screws, tacks, slings, drug delivery devices, wound dressings, woven devices, non-woven devices, braided devices, and other implants. In certain embodiments, the medical device is formed from one or more filaments. The filaments can be knitted, braided, woven or non-woven. In a particularly useful embodiment, the medical device is a braided suture.

The medical device can be formed from any sterilizable material that has suitable physical properties for the intended use of the medical device. The medical device can be bioabsorbable or non-bioabsorbable. Some specific examples of suitable absorbable materials which may be utilized to form the medical device include trimethylene carbonate, caprolactone, dioxanone, glycolic acid, lactic acid, glycolide, lactide, homopolymers thereof, copolymers thereof, and combinations thereof. Some specific examples of suitable non-absorbable materials which may be utilized to form the medical device include polyolefins, such as polyethylene, polypropylene, copolymers of polyethylene and polypropylene, and blends of polyethylene and polypropylene.

Figure 1:
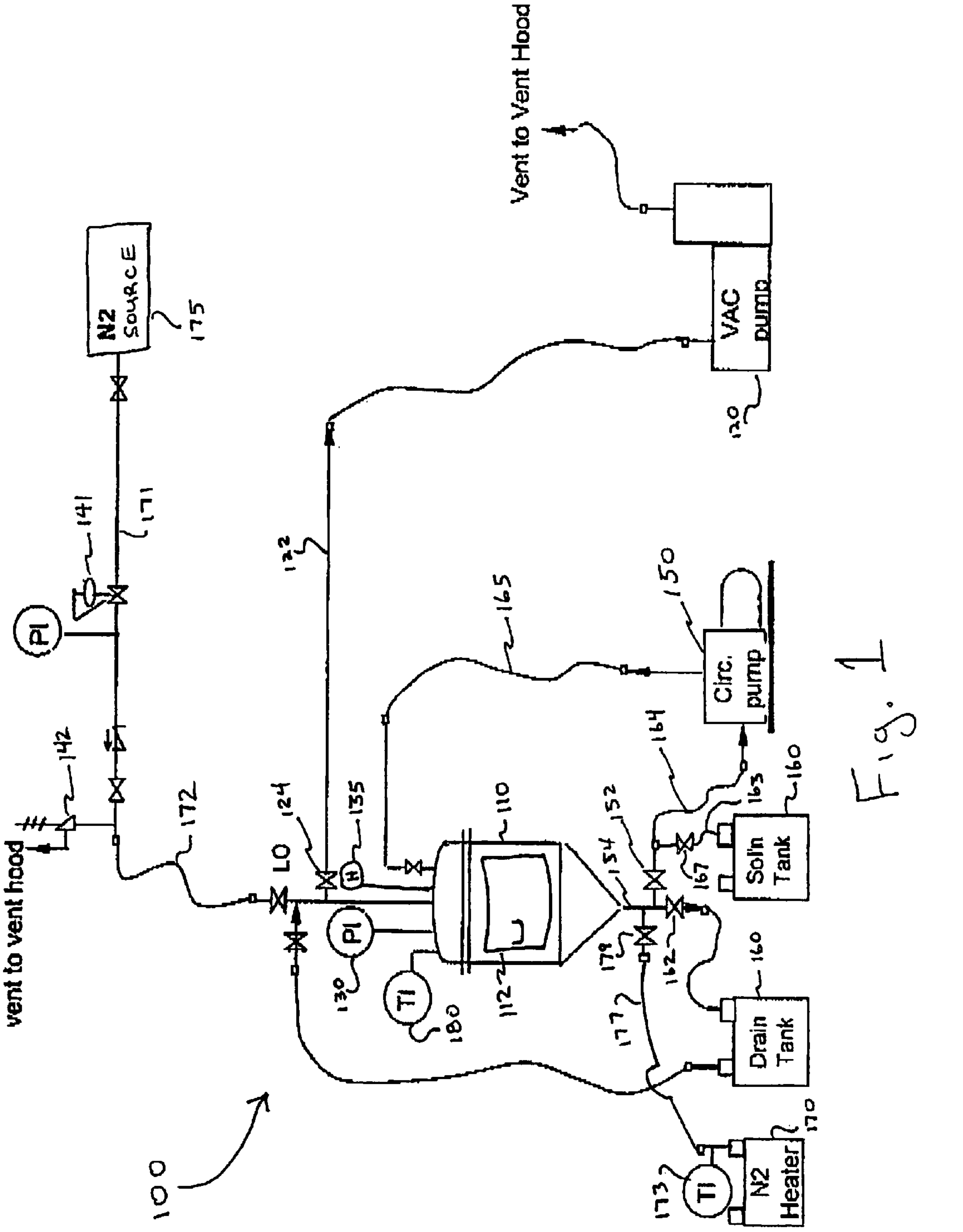
FIG. 1 illustrates one embodiment of a coating apparatus suitable for coating a medical device in accordance with this disclosure.
Figure 2:
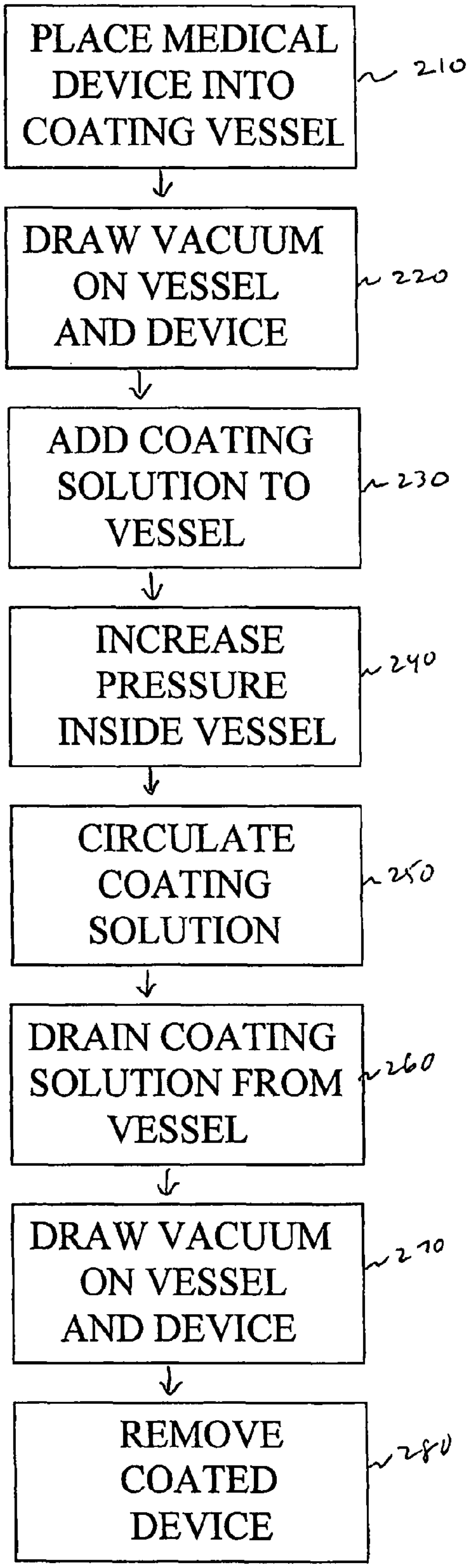
FIG. 2 is a flowchart illustrating a method of forming a coating onto a surface of a medical device in accordance with one embodiment described herein.

Referring now to FIG. 1, one embodiment of an apparatus 100 for coating a medical device includes a coating vessel 110 into which a medical device to be coated is placed. (See, step 210 in FIG. 2.) Vessel 110 includes a sealable door 112 through which one or more medical devices to be coated can be placed into vessel 110 and the coated medical device can be removed from vessel 110. While the medical device can be placed into the coating vessel 110 in any manner or position, the greater the surface area of the medical device that is accessible to the coating solution, the more thorough a coating the medical device will receive. Thus, a rack (not shown) adapted to hold the one or more medical devices may be placed within vessel 110. In some embodiments, sutures wound on a spool or a rack are placed within vessel 110.

The interior of vessel 110 can be advantageously made from or lined with a material that is non-reactive with the medical device and the coating composition. Such non-reactive materials include stainless steel, glass and the like. It is also contemplated that the interior of vessel 110 can be passivated to make the interior surface less reactive. Passivation techniques are within the purview of those skilled in the art.

Once the coating vessel contains the medical device, the medical device is subjected to reduced pressure. (See, step 220 in FIG. 2.) The pressure within the vessel 110 can be reduced by any means known to one skilled in the art. In the embodiment shown in FIG. 1, a vacuum pump 120 is connected to the coating vessel 110. The vacuum pump 120 can be used to withdraw air from the coating vessel 110 through line 122 if valve 124 is open. The pressure within vessel 110 can be reduced to a pressure in the range of about 740 to 1 mmHg, more typically in the range of 100 to 10 mmHg. The pressure inside the coating vessel 110 is monitored during this step and other steps of the coating process by pressure indicator 130. Providing a reduced pressure environment within vessel 110 prepares the medical device placed therein to better receive the coating composition, especially where the medical device includes small interstices. In addition, hygrometer 135 can be provided to monitor the level of humidity in vessel 110 during this and other steps of the process.

Optionally, an inert gas, (such as, for example xenon, neon, argon or nitrogen), can be flowed through the vessel during the evacuation step. To this end, line 172 connects vessel 110 to a nitrogen source 175. An inert gas flush will help remove any air from vessel 110, thereby assisting in drying the medical device and insuring a non-reactive environment for the coating process.

Once the desired pressure is attained within vessel 110, a coating composition is introduced into vessel 110. (See, step 230 in FIG. 2.) The coating composition can be added to the coating vessel 110 in any manner within the purview of one skilled in the art. In the embodiment depicted in FIG. 1, a coating composition is stored in reservoir 160 and enters the coating vessel 110 via lines 163, 164, 165 once valve 167 is opened and with the assistance of pump 150. The amount of coating composition added to the coating vessel 110 should be sufficient to cover the medical devices to be coated. As those skilled in the art will appreciate, because medical devices to be coated can vary in size and surface area, and the manner in which the medical devices to be coated can be positioned within the vessel in various ways (e.g., on racks, spools, etc.), the amount of the coating solution added to the vessel will vary accordingly.

Any coating composition known to be used to coat medical devices may be applied to a medical device using the present methods and apparatus. The coating composition can be a solution, dispersion, emulsion containing, for example, one or more polymeric materials and/or one or more bioactive agents.

In some embodiments, the coating composition includes a polymer, or a combination of polymers. The polymer is most suitably biocompatible, including polymers that are non-toxic, non-inflammatory, chemically inert, and substantially non-immunogenic in the applied amounts. The polymer may be either bioabsorbable or biostable. A bioabsorbable polymer breaks down in the body. Bioabsorbable polymers are gradually absorbed or eliminated by the body by hydrolysis, metabolic process, bulk, or surface erosion. Examples of bioabsorbable materials include but are not limited to polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly (iminocarbonate), copoly(ether-esters), polyalkylene oxalates, polyphosphazenes, polyiminocarbonates, and aliphatic polycarbonates. Biomolecules such as heparin, fibrin, fibrinogen, cellulose, starch, and collagen are typically also suitable. A biostable polymer does not break down in the body, and thus a biostable polymer is present in the body for a substantial amount of time after implantation. Examples of biostable polymers include Parylene™, Parylast™, polyurethane (for example, segmented polyurethanes such as Biospan™), polyethylene, polyethlyene teraphthalate, ethylene vinyl acetate, silicone, polyethylene oxide, and polytetrafluoroethylene (PTFE).

The coating composition may also include a solvent. Suitable solvents include, but are not limited to, organic solvents, volatile solvents, alcohols, e.g., methanol, ethanol, propanol, chlorinated hydrocarbons (such as methylene chloride, chloroform, 1,2-dichloro-ethane, 1,1,2-trichloro-ethane), aliphatic hydrocarbons (such as hexane, heptene, ethyl acetate), aromatic solvents (such as toluene, benzene, xylene) and combinations thereof.

In some embodiments, the coating compositions of the present disclosure may also include a fatty acid component that contains a fatty acid or a fatty acid salt or a salt of a fatty acid ester. Suitable fatty acids may be saturated or unsaturated, and include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, particularly those having from about 12 to 22 carbon atoms, and mixtures thereof. Fatty acid salts including the calcium, magnesium, barium, aluminum, and zinc salts of stearic, palmitic and oleic acids may be useful in some embodiments of the present disclosure. Particularly useful salts include commercial "food grade" calcium stearate which consists of a mixture of about one-third $C_{16}$ and two-thirds $C_{18}$ fatty acids, with small amounts of the $C_{14}$ and $C_{22}$ fatty acids.

Suitable salts of fatty acid esters which may be included in the coating compositions applied in accordance with the present disclosure include calcium, magnesium, aluminum, barium, or zinc stearoyl lactylate; calcium, magnesium, aluminum, barium, or zinc palmityl lactylate; calcium, magnesium, aluminum, barium, or zinc olelyl lactylate; with calcium stearoyl-2-lactylate (such as the calcium stearoyl-2-lactylate commercially available under the tradenameVERV from American Ingredients Co., Kansas City, Mo.) being particularly useful. Other fatty acid ester salts which may be utilized include those selected from the group consisting of lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, and francium olelyl lactylate.

Where utilized, the amount of fatty acid component can range in an amount from about 5 percent to about 50 percent by weight of the total coating composition. Typically, the fatty acid component may be present in an amount from about 10 percent to about 20 percent by weight of the total coating compositions.

In some embodiments, the coating composition contains one or more bioactive agents. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent which provides a therapeutic or prophylactic effect, a compound that affects or participates in tissue growth, cell growth, cell differentiation, a compound that may be able to invoke a biological action such as an immune response, or could play any other role in one or more biological processes.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Suitable antimicrobial agents which may be included as a bioactive agent in the bioactive coating of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the coating composition applied in accordance with the present disclosure include: local anesthetics; nonsteroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

A single bioactive agent may be utilized to form the coating composition or, in alternate embodiments, any combination of bioactive agents may be utilized to form the coating composition applied in accordance with the present disclosure.

After the coating composition is introduced into coating vessel 110, the pressure inside the coating vessel 110 is increased. (See, step 240 in FIG. 2.) The pressure can be raised using any technique within the purview of one skilled in the art. In the embodiment shown in FIG. 1, inert gas (nitrogen) from source 175 is introduced into the coating vessel 110 via lines 171, 172 to increase the pressure within vessel 110. Pressure control valve 141 is used for controlling the flow of the inert gas through line 171 and a pressure safety valve 142 is used to release pressure from the line when the pressure in the line is higher than needed or for safety purposes.

It is also contemplated that in other embodiments, the pressure within vessel 110 can be raised using a structure (not shown) that provides a static head of the coating composition. Techniques for producing pressure using a static head are within the purview of those skilled in the art.

The pressure can be increased to any super-atmospheric level. Thus, the pressure may range from about 761 mmHg to 2 atmospheres or more. Typically, pressures in the range of from about 770 to about 900 mmHg are used. The pressure inside the vessel is monitored and measured by the pressure indicator 130.

The increased pressure inside the coating vessel 110 will also increase the temperature inside the coating vessel 110. The temperature is measured and monitored by the temperature indicator 180 that is also directly attached to the coating vessel 110.

Once the system is pressurized, the coating composition is circulated. (See, step 250 in FIG. 2). The coating composition can be circulated in any manner known to one skilled in the art. In the embodiment shown in FIG. 1, pump 150 is used to circulate the coating composition. The coating composition exits vessel 110 through line 154, and with valve 152 open passes through line 164 and is pumped by pump 150 through line 165 back into vessel 110.

The coating composition is circulated for a predetermined amount of time ranging from about 10 seconds to about 60 minutes. Typically, the coating composition is circulated for about 2 minutes to about 10 minutes.

Once the predetermined amount of time expires, the coating composition is drained from vessel 110. (See, step 260 in FIG. 2.) Before emptying the excess coating composition, the pressure inside the coating vessel can advantageously be returned back to atmospheric pressure. Any method within the purview of those skilled in the art may be to drain the coating composition from the vessel 110. For example, the excess coating composition can be drained from the coating vessel 110 using gravity. In the embodiment shown in FIG. 1, coating composition flows through line 154 through open valve 162 into drain tank 160.

Following the removal of the excess coating composition, the coated medical device is dried. The drying of the coated medical device can be done using any drying method within the purview of those skilled in the art. For example, the pressure within vessel 110 can be again reduced. (See, step 270 in FIG. 2.) Vacuum pump 120 is turned on, thereby, sweeping the medical device with air or inert gas. Optionally, heated inert gas may be swept over the coated medical device. For example, as shown in the embodiment of FIG. 1, heater 170 warms inert gas which is pulled by vacuum pump 120 through line 177 and open valve 179 into vessel 110 where it passes over the coated medical device. The heater contains its own temperature indicator 173 to measure and monitor the temperature of the gas before entering the coating vessel 110.

It is also contemplated that a solvent tank and/or master batch of coating composition (not shown) can be provided to refresh the coating composition to ensure the desired concentrations of coating components are maintained in the coating composition. For example, if solvent volatilizes and is vented trough a hood or to the atmosphere, additional solvent can be mixed into the coating composition to maintain the desired formulation.

It is also contemplated that a control system (e.g., a computer control system (not shown)) can be provided to automate the operation of the present coating apparatus.

It will be understood that various modifications may be made to the embodiments described herein. Therefore, the above description should not be construed as limiting, but merely as exemplifications of preferred embodiments. Those skilled in the art will envision other modifications within the scope and the spirit of the claims appended hereto.

What is claimed is:

1. A method of coating a medical device, the method comprising the steps of:

placing a medical device into a coating vessel;

reducing pressure within the coating vessel adding a coating composition to the coating vessel in an amount sufficient to contact the medical device;

increasing pressure in the coating vessel to a predetermined super-atmospheric pressure;

circulating the coating composition into and out of the coating vessel for a predetermined amount of time;

draining the coating composition from the coating vessel;

drying the coated medical device while positioned within the coating vessel; and removing a coated medical device from the coating vessel.

2. The method of claim 1 wherein the medical device is selected from the group consisting of sutures, staples, meshes, stems, grafts, clips, pins, screws, tacks, slings, drug delivery devices, wound dressings, and combinations thereof.

3. The method of claim 1 wherein the medical device a multifilament suture.

4. The method of claim 1 wherein the step of reducing pressure in the coating vessel comprises reducing the pressure to a range from about 740 to about 1 mmHg.

5. The method of claim 1 wherein the step of reducing pressure in the coating vessel comprises reducing the pressure to a range from about 100 to about 10 mmHg.

6. The method of claim 1 wherein the coating composition is bioabsorbable.

7. The method of claim 6 wherein the bioabsorbable coating composition comprises materials selected from the group consisting of polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, aliphatic polycarbonates, heparin, fibrin, fibrinogen, cellulose, starch, collagen and combinations thereof.

8. The method of claim 1 wherein the coating composition is biostable.

9. The method of claim 8 wherein the biostable coating composition comprises materials selected from the group consisting of polyurethane, polyethylene, polyethlyene teraphthalate, ethylene vinyl acetate, silicone, polyethylene oxide, polytetrafluoroethylene and combinations thereof.

10. The method of claim 1 wherein the coating composition comprises a fatty acid salt.

11. The method of claim 1 wherein the coating composition further comprises a bioactive agent.

12. The method of claim 1 wherein the step of increasing pressure in the coating vessel comprises increasing the pressure to a range of about 761 mmHg to about 2 atmospheres.

13. The method of claim 1 wherein the step of increasing pressure in the coating vessel comprises increasing the pressure to a range of about 770 mmHg to about 900 mmHg.

14. The method of claim 1 wherein the step of circulating the coating composition for a predetermined amount of time comprises circulating the coating from about 10 seconds to about 60 minutes.

15. The method of claim 1 wherein the step of circulating the coating composition for a predetermined amount of time comprises circulating the coating from about 2 minutes to about 10 minutes.

16. The method of claim 1 wherein the step of drying the medical device comprises drawing a gas through the coating vessel over the medical device having the coating composition on at least a portion thereof.

17. The method of claim 16 wherein the step of drawing a gas through the coating vessel comprises drawing heated nitrogen gas through the coating vessel.

18. A method of coating a medical device, the method comprising the steps of:

placing a medical device into a coating vessel;

reducing pressure within the coating vessel to a range from about 100 to about 10 mmHg adding a coating composition to the coating vessel in an amount sufficient to contact the medical device;

increasing pressure in the coating vessel to a range of about 761 mmHg to about 2 atmospheres;

circulating the coating composition into and out of the coating vessel for a predetermined amount of time;

draining the coating composition from the coating vessel;

drying the coated medical device while positioned within the coating vessel; and removing a coated medical device from the coating vessel.

* * * * *